United States Patent [19]

Markham

[11] Patent Number: 4,555,243
[45] Date of Patent: Nov. 26, 1985

[54] FLEXIBLE AND PROTECTIVE GUIDE DEVICE FOR USE WITH ASPIRATING NEEDLES

[76] Inventor: Charles W. Markham, 667 Snug Island, Clearwater Bch., Fla. 33515

[21] Appl. No.: 586,036

[22] Filed: Mar. 5, 1984

[51] Int. Cl.[4] .............................................. A61B 10/00
[52] U.S. Cl. ................................... 604/263; 604/164; 604/171; 604/179; 604/272; 128/77; 128/DIG. 26; 128/329 R; 128/361
[58] Field of Search ............... 604/263, 116, 158, 161, 604/162, 163, 164, 170, 171, 174, 177, 179, 263, 264, 271, 272, 282, 292, 117; 128/329, 361, 77, DIG. 26

[56] References Cited

U.S. PATENT DOCUMENTS

| | | | |
|---|---|---|---|
| 2,700,385 | 1/1955 | Ortiz | 604/263 |
| 2,811,969 | 11/1957 | Shubert | 128/329 R |
| 2,880,724 | 4/1959 | Velarde | 604/263 |
| 3,042,030 | 7/1962 | Read | 604/57 |
| 3,572,335 | 3/1971 | Robinson | 604/57 |
| 3,796,211 | 3/1974 | Kohl | 604/171 |
| 4,023,559 | 5/1977 | Gaskell | 604/158 |
| 4,157,709 | 6/1979 | Schuster et al. | 604/158 |
| 4,194,504 | 3/1980 | Harms et al. | 604/164 |
| 4,252,131 | 2/1981 | Hon et al. | 604/275 |

FOREIGN PATENT DOCUMENTS 0839507 6/1960 United Kingdom ................ 604/263

Primary Examiner—C. Fred Rosenbaum
Assistant Examiner—Mark Rooney
Attorney, Agent, or Firm—Ronald E. Smith; Harold D. Shall

[57] ABSTRACT

An elongated aspirating needle guide made of flexible plastic such as polypropylene and an elongated flexible aspirating needle having a medial plastic tubular portion made of PVC and terminating at ends with metallic needle portions. The guide has a base portion and an upper portion and has an elongated opening through the upper portion which receives the elongated aspirating needle. The opening in the elongated guide terminates short of the distal end of the guide. The base portion of the guide is wider than the upper portion and the base portion also extends distally from the upper portion. The distal end of the base portion is adapted to overlie the inner surface of the operator's finger adjacent the distal end of the finger of the operator who will utilize the device so that the flexible base portion protects the inner surface of the finger while being sufficiently thin enough to allow tactile palpation to be conducted through the distal end of the base portion. When the needle projects from the distal end of the elongated opening, it will impinge upon the distal end of the base portion allowing the operator to be protected from the needle while at the same time directing the needle into the desired palpated area from which a biopsy will be taken.

7 Claims, 7 Drawing Figures

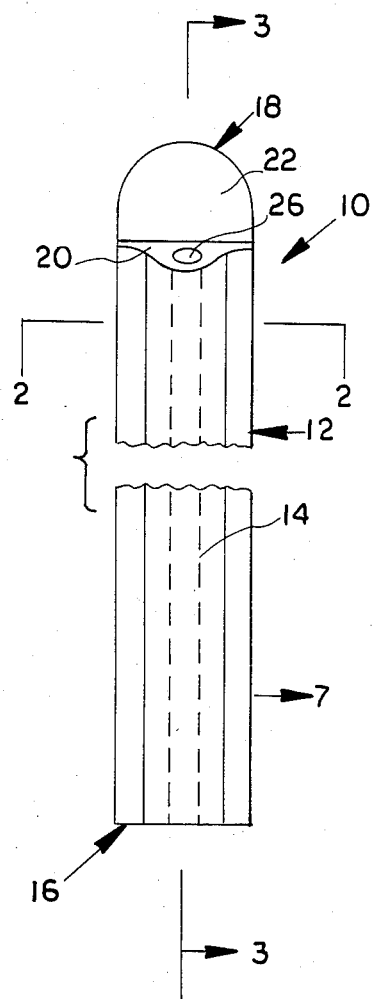
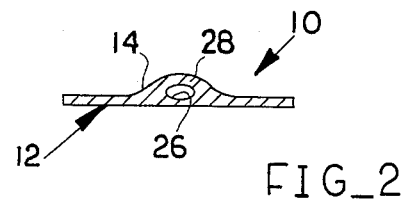
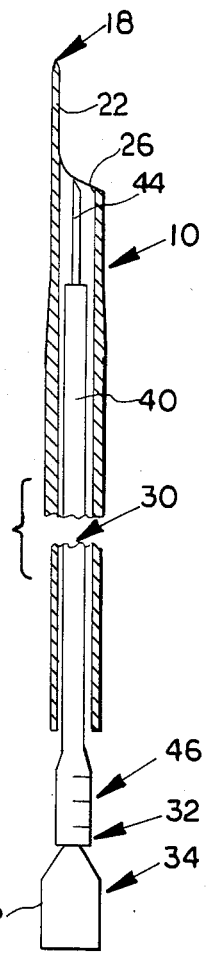
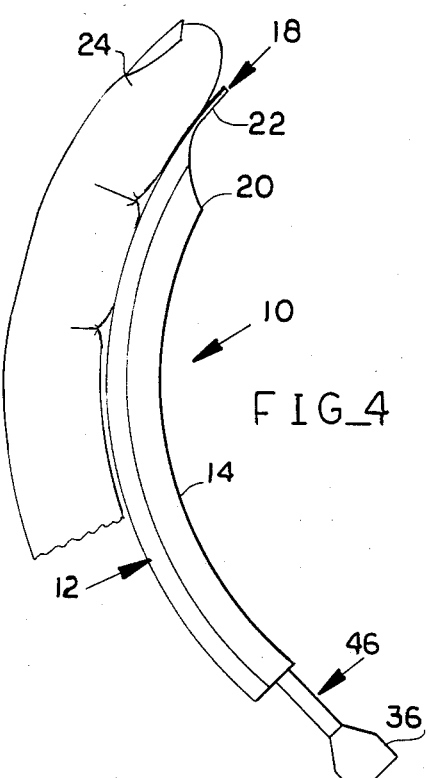
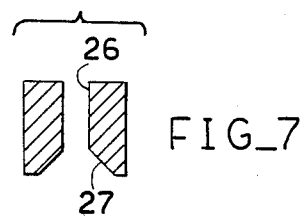
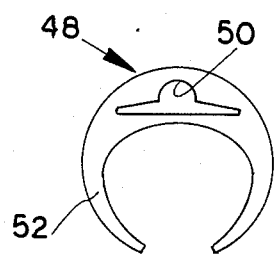
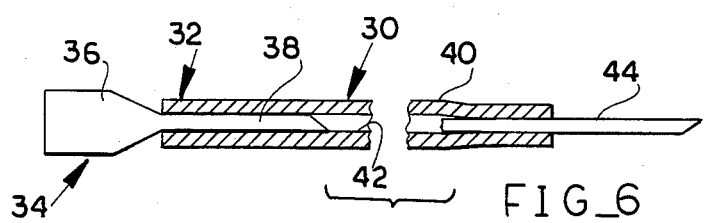

FLEXIBLE AND PROTECTIVE GUIDE DEVICE FOR USE WITH ASPIRATING NEEDLES

BACKGROUND OF THE INVENTION

1. Field of the Invention

This invention relates to needle guides generally and more particularly to an elongated needle guide made of flexible plastic and having a flexible protective distal end which provides for tactile palpation through the protective end.

2. Description of the Prior Art

Devices as described above find use in a diagnostic procedure described in an article by Josef Zajicek, M.D., F. I. A. C., entitled "Transrectal Aspiration Biopsy of the Prosate" which appears at pages 568–573 of a book entitled "Tutorial Proceedings", Volume IV, Number 1, 1976, Compendium of Diagnostic Cytology, Fourth Edition, Copyright 1976 by the Tutorials of Cytology, 4841 South Maryland Avenue, Chicago, Ill. 60637.

Such a device is also seen on page 131 in FIG. 66 of a book entitled "Monograms in Clinical Cytology, Volume 7".

In the Zajicek article is described a device known in the art as a Franzen Prostator which includes a syringe, an elongated needle, and a needle guide. The needle guide is an elongated metallic tube adapted to lie along the inner surface of the index finger with the proximal end extending to the heel of the hand. The proximal end is of an enlarged funnel shape to facilitate the insertion into the guide of the elongated aspiration needle. The distal end of the tube is secured in a steering ring, with the metallic tube terminating and open at the distal end of the steering ring. The palpating finger is inserted into and through the steering ring to project therebeyond so that during use of the biopsy device, this finger can be used to palpate the prostate, find the desired biopsy location, at which time the finger is moved out of the way so that the aspirating needle can be pushed from the distal end of the metallic tube of the needle guide and into the biopsy area of the prostate. At this time a sample can be aspirated into the needle by a suitable syringe conventionally attached to the proximal end of the needle. A metal plate is adjustably secured to the metallic tube intermediate its ends and adapted to rest in the palm of the hand to assist in supporting the instrument during the use thereof.

The metallic tube described above is fairly substantial and therefore only moderately flexible, and provides no tactile feel through the tube. Further, the tube ends at the steering ring so that the operator's finger projecting beyond the steering ring is not protected by the steering ring or the steel tube when the aspirating needle is projected out of the distal end of the tube. Additionally, since there is no protection of the projecting finger, the finger must be moved aside during sample taking with the possibility of missing the desired palpated area with the projecting needle. Further, there is no possibility of tactile palpation immediately adjacent to the tube opening since the steering ring holds the finger away from the suspect area immediately adjacent the end of the steering ring.

It is an object of this invention to provide an elongated needle guide which is flexible and which provides a tactile protective arrangement for the operative finger on which it is utilized, so that tactile feel of the biopsy location and of the aspirating needle is possible at the time of insertion of the aspirating needle into the biopsy location.

It is another object of this invention to provide a flexible elongated needle guide which provides for stable engagement with the guiding finger.

SUMMARY OF THE INVENTION

The present invention accomplishes the above objects. It includes an elongated flexible and protective guide device made of relatively thin plastic. A plastic which has been found to give satisfactory results is polypropylene of the type, texture and hardness generally used in small plastic drinking or stirring straws; however, it is assumed that other materials such as polyvinylchloride, polycarbonate, high density polyethylene or linear polyester can be substituted for polypropylene if formulated to have the appropriate hardness, texture and flexibility. The protective device has a relatively wide base to give it lateral stability and provide for a broad base support along the inner curve of the index finger upon which it is usually carried during palpation and sample aspiration.

From the middle of the base projects an outer portion, in a direction which would be opposite to the side of the base that would engage the index finger, which outer portion contains an elongated opening, extending for the length thereof, for receiving an elongated aspirating needle. At the distal end of the guide device, the hollow outer portion of the guide device is not present so that only the base portion of the guide device is present. The distal end of the base portion is adapted to overlie the inner surface of the index finger adjacent to the distal end of the finger. The distal end of the base portion is relatively thin, (a thickness of 0.006–0.010 inches has been found to be satisfactory). The distal end of the index finger can have tactile sensation of the suspect area through the plastic, and when the needle is projected through the elongated opening, the distal end of the base portion will give protection to the finger and can be used to direct the needle into the adjoining biopsy location, and the finger tip need not be moved aside while needling the biopsy location. Because of the tactile sensation available through the distal end of the plastic, and actual location and penetration of the needle can be identified.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a plan view of a flexible guide according to this invention;

FIG. 2 is a cross sectional view taken along the line 2—2 in FIG. 1;

FIG. 3 is a cross sectional view of the invention of FIG. 1 taken along the line 3—3 of FIG. 1 and showing an aspiration needle in the guide;

FIG. 4 is a side elevational view of the invention of FIG. 1 with the aspirating needle in the guide and showing the guide in its operative position along the inner surface of a portion of the index finger;

FIG. 5 is a front elevational view of a supporting ring which can be used with the guide of this invention;

FIG. 6 is a longitudinal sectional view of a flexible needle for use with the invention; and FIG. 7 is a cross sectional view taken along the line 7—7 in FIG. 1 but showing a modified opening at the proximal end of the guide.

Similar reference numerals refer to similar parts throughout the several views of the drawings.

DETAILED DESCRIPTION OF THE PREFERRED EMBODIMENT

Referring now to the drawings, and more particularly to FIGS. 1 and 2, a guide device is shown generally at 10 and is made from a suitable flexible plastic, such as polypropylene of the texture, hardness and flexibility generally used in small drinking straws. The guide device 10 includes a base portion 12 from which an outer portion 14 projects. As is evident from the above-referred to article by Zajicek, the direction which the outer portion 14 projects from the base 12 when the guide device 10 is in its usual operative position is an upward direction, and such direction will so be referred to herein.

The outer portion 14 commences at the proximal end 16 of the guide device 10, while, as seen in FIG. 1, the outer portion 14 terminates short of the distal end 18 of the guide device; such termination being in the form of a sloping shoulder 20. Accordingly, the flat distal end portion of the base portion 12, which is shown at 22, does not have the outer portion projecting therefrom, as can also be seen in FIGS. 3 and 4. The length of the guide device 10 should be such that when the distal end 18 is positioned adjacent to the distal end of the operator's finger 24 (as seen in FIG. 4) the proximal end 16 of the guide device will be located in the general area of the heel of the hand (not shown).

With the device as shown in the drawings, the flat distal end portion 22 (which preferably has a rounded extremity for patient comfort) is approximately 0.375 inches long, while the base portion 12 is approximately 0.300 inches wide, the thickness of the base portion laterally of the outer portion 14 and also the thickness of the flat distal end portion 22 is approximately 0.006 inches (however; thicknesses as great as 0.010 inches have been found satisfactory) and the upper portion 14 has an opening 26 which extends for the full length thereof, which opening is approximately 0.100 inches in diameter. The wall 28 surrounding the opening 26 is also approximately the same thickness as the base portion.

As an alternate embodiment of the invention shown in FIG. 1, FIG. 7 shows the proximal end of the opening 26' having a slight taper 27 therein to facilitate the insertion of an elongated aspirating needle 30 as hereinafter more fully described.

Referring once again to the first embodiment of FIGS. 1-6 and particularly to FIG. 6, an elongated aspiration needle 30 suitable for use with the guide of this invention is shown. The needle used with the Franzen Prostator described in the above-referred to article by Zajicek, is made entirely of stainless steel, and, as such, is fairly expensive as is the stainless steel prostator. The guide and needle of the instant invention is intended as a throw away instrument, and as such is constructed of simple inexpensive plastic material except for the two ends of the elongated needle 30.

Referring to FIGS. 3, 4 and 6 and particularly to FIG. 6, the proximal end 32 of the elongated needle 30 consists of a standard throw away needle 34 having a conventional hollow plastic hub 36. Conventionally secured to and projecting from the hub 36 is the elongated metallic hollow stainless steel tube portion 38 of the needle 34. An elongated plastic tube 40 forms the medial portion of the elongated needle 30. A plastic which has been found satisfactory for the tube 40 is polyvinylchloride. The length of the tube 40 can be selected as more fully described hereinafter.

The steel tube portion 38 of the needle 34 is telescoped into the central opening 42 at the proximal end of the tube 40 and secured therein by a suitable PVC adhesive; the insertion being sufficient so that the plastic hub 36 of the needle 34 abuts the proximal end of the plastic tube 40. A size 21; 22 or 23 needle has been found satisfactory for the needle 34; these sizes being sufficiently thin so that when mounted in the tube 40, the mounted needle in the tube is still flexible, yet is of sufficient diameter to sufficiently stiffen the plastic tube 40 so that when the proximal end of the aspirating needle 30 is manipulated, the needle 34 prevents undue flexing of the assembly. The opening 42 in the tube 40 is approximately 0.035 inches in diameter so that either a size 21 (0.032 inches diameter) or size 22 (0.028 inches diameter) or size 23 (0.025 inches diameter) can be secured therein. The outside diameter of the plastic tube 40 is approximately 0.090 inches so that it may be telescopically received in a guiding manner for relative axial movement in the opening 26 in the guide device 10. It should be understood that the needles and the sizes of the tube and the sizes of the opening in the guide have been selected for the particular materials and desired scope of operation of this application; however, the sizes and materials may be deviated from without deviating from the concept of this invention.

At the distal end of the plastic tube 40 is secured by a suitable adhesive the steel tube portion 44 of a hubless needle. The tube portion 44 is about two inches long with approximately one-half the length within the tube 40 and one-half of the length projecting distally therefrom. The steel tube portion is preferably from a size 21, 22 or 23 needle, so that it is sufficiently flexible so that when it protrudes from the opening 26 and strikes the flat distal end portion 22 of the guide 10, it may be deflected into the tissue from which a biopsy is to be taken. Further, a needle of these sizes when mounted in the plastic tube 40, which is in turn mounted in the plastic guide 10, does not inhibit the flexibility of the guide 10 and the aspirating needle assembly 30. FIG. 4 shows how this assembly is mounted to the inner surface of a gloved finger, shown fragmentarily at 24; (usually the index finger) of the operator. It has been found desireable to place a cot over the end of the finger and the adjacent end of the guide to securedly attach the guide to the finger. In FIGS. 3 and 4, the aspirating needle is in its withdrawn position so that the steel needle 44 at the distal end thereof is not projecting from the distal end of the opening 26 in the guide 10.

FIG. 4 shows how the flat distal end portion 22 of the distal end 18 of the base portion 12 overlies the inner surface of the distal end of the operator's finger to protect the same when the needle is projecting from the opening 26. When the needle projects from the opening 26 it will penetrate the cot (not shown) which overlies the same.

The flat distal end portion 22 being made of the plastic as hereinabove described, provides the operator with tactile palpation by the inner surface of the finger adjacent the distal end of the finger mounting the guide device 10, and, as the distal end of the steel tube portion 44 of the needle 30 is projected from the opening 36 it will slide along the flat distal end portion 22 of the guide 10 and allow the operator to use this finger to direct the needle to the palpated desired location while continuing his palpating tactile direction of the needle into the desired biopsy area.

The needle 34 at the proximal end of the aspirating needle 30, by projecting into the plastic tube 40, provides flexible rigidity to the portion of the aspirating needle extending out of the proximal end of the guide 10. A suitable syringe (not shown), for example one shown in U.S. Pat. No. 3,819,091, or one shown in my co-pending application Ser. No.: 567,734, filed Jan. 3, 1984, can be inserted into the hub 36 of the needle 34. The flexible rigidity of the aspiration needle 30 resulting from the steel tube 38 of the needle 34 being in the plastic tube 40 allows the syringe to be advanced and, in turn, to advance the needle 30 into the guide 10 without undue flexure of the plastic tube 40 at this location. When the distal end of the needle 30 is within the guide 10, the amount of the plastic tube 40 extending from the guide 10 is about two inches with the length of the steel tube portion 38 of the needle 34 being approximately two inches. The length of the plastic tube 40 is selected to provide this desired amount of projection.

It is also contemplated that marks, shown at 46, be scribed on the periphery of the proximal end of the plastic tube 40 so that the operator can tell at a glance how far the needle 44 is projecting from the distal end of the opening 26. The space between the marks can be colored so that this determination can be made by a mere glance.

Referring now to FIG. 5, a supporting ring 48 is shown for use with the guide 10. The ring 48 has an opening 50 which is dimensioned to closely telescopically register with the guide 10 and a finger encircling portion 52 adapted to encircle the operator's finger. This ring is to be placed on the guide and the finger at a location away from the distal end of the finger so as not to prevent the tactile contact between the finger and the flat distal end portion 22 of the guide 10. The above-referred to cot can be placed over the guide and the supporting ring 48 to provide intimate secure relationship between the guide and the finger.

The base portion 12 which projects laterally beyond the upper portion 14 (the projecting portion being hereinafter sometimes referred to as flanges), when held against the finger by the cot and/or the guide provides a stable and secure connection between the guide and the operator's finger. The flexibility of the guide and the aspirating needle allow the finger mounting the same to be easily inserted into a body cavity, to obtain a biopsy as, for example, discussed in the above-referred to Zajicek article concerning transrectal aspiration biopsy of the prostate.

Although the description relates to presently preferred embodiments, numerous modifications may be made without departing from the spirit of the invention as defined in the claims.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An elongated flexible and protective guide device for mounting on an operator's finger and for use with a flexible elongated aspirating needle comprising a flexible elongated tubular element having a proximal and a distal end and an elongated opening therethrough which telescopically receives said needle, a pair of flexible elongated flanges secured to said tubular element, having a length substantially equal to the length of said tubular element and projecting laterally beyond said tubular element to stabilize it against rolling displacement, and said guide device including a flexible distal base portion secured to the remainder of said guide device, said base portion extending distally beyond said tubular element and being made of a flexible plastic having a thickness between about six thousandths of an inch and one hundredth of an inch, providing for tactile palpation therethrough, which thinness allows appreciation of a needle tip presence, while being thick enough to allow for sliding protective engagement with the tip of the aspirating needle, said base portion being positioned to lie between the projecting needle and the operator's finger, the amount of flexibility of said needle, tubular element, flanges, and base portion being sufficient to allow the operator's finger to bend during said palpation by an amount that allows said operator to feel an abnormal growth or swelling on the area being inspected with said operator's fingertip, said device permitting said operator to continue palpating said growth or enlarged area while simultaneously taking a sample thereof with said aspirating needle, there being no need for the fingertip of the operator to withdraw from the area being sampled, whereby the operator's fingertip can guide the needle into a nodule and can feel the needle entering the nodule while being protected from a puncture wound caused by said needle.

2. A guide device according to claim 1 wherein said elongated flanges and said base portion are uniplanar.

3. A guide device according to claim 2, wherein the plane of said elongated flanges and said base portion lie below said elongated opening.

4. A guide device according to claim 3, wherein said flanges, said tubular element, and said base portion are molded unitarily.

5. A guide device according to claim 1, wherein said tubular element, said flanges and said base portion are of a one piece molded construction.

6. A flexible and protective guide device made of plastic for use with an elongated aspirating needle and for mounting on an operator's finger, comprising, an elongated flexible base portion having a proximal and a distal end, a flexible outer portion secured to said base portion and projecting upwardly therefrom, said outer portion having a distal and a proximal end with the distal end thereof terminating short of the distal end of said base portion so that said base portion projects distally therebeyond, said outer portion having an elongated opening therethrough for telescopically receiving said aspirating needle, said base portion having a length substantially equal to the length of said outer portion and extending laterally beyond said outer portion to stabilize the same against rolling displacement and adapted to be mounted against the inner surface of an operator's finger adjacent the distal end thereof and said projecting distal end of said base portion being thin and flexible enough to allow for tactile palpation through the same by the inner surface of the operator's finger, while having a thickness between about six thousandths of an inch to one hundredth of an inch to prevent penetration by the aspirating needle when it projects from said elongated opening, and having said thickness to deflect the needle's point when said point abuts said projecting distal end of said base portion, the amount of flexibility of said base portion and said outer portion being sufficient to allow said operator's finger to bend during said palpation by an amount that allows said operator to feel an abnormal growth or swelling of the area being inspected through said hard but thin projecting distal end, said device permitting said operator to continue palpating said growth or enlarged area while simultaneously taking a sample thereof with said aspirating needle.

7. A device according to claim 6, wherein said base portion and said outer portion are molded integrally.

* * * * *